United States Patent [19]

Rosheim

[11] Patent Number: 5,239,883

[45] Date of Patent: Aug. 31, 1993

[54] MODULAR ROBOT WRIST

[76] Inventor: Mark E. Rosheim, 1565 St. Paul Ave., St. Paul, Minn. 55116

[21] Appl. No.: 765,957

[22] Filed: Sep. 26, 1991

[51] Int. Cl.⁵ .................... B25J 17/02; G05G 11/00
[52] U.S. Cl. .................. 74/479 BP; 901/29
[58] Field of Search .............. 74/479; 901/29, 28

[56] References Cited

U.S. PATENT DOCUMENTS

| | | | |
|---|---|---|---|
| 1,325,702 | 12/1919 | Schelb | 464/125 |
| 3,046,840 | 7/1962 | Barcus | 74/479 |
| 3,602,059 | 8/1971 | Jupe | 74/469 |
| 4,073,201 | 2/1978 | Taylor et al. | 74/479 X |
| 4,194,437 | 3/1980 | Rosheim | 92/120 |
| 4,229,136 | 10/1980 | Panissidi | 901/29 X |
| 4,296,681 | 10/1981 | Rosheim | 92/122 |
| 4,628,765 | 12/1986 | Dien et al. | 901/29 X |
| 4,686,866 | 8/1987 | Rosheim | 74/479 |
| 4,723,460 | 2/1988 | Rosehim | 74/479 |
| 4,729,253 | 3/1988 | Rosheim | 74/479 |
| 4,739,241 | 4/1988 | Vachtsevanos et al. | 901/29 X |
| 4,748,867 | 6/1988 | Susnjara | 74/479 |
| 4,804,220 | 2/1989 | Rosheim | 294/111 |
| 4,805,477 | 2/1989 | Akeel | 901/29 X |
| 4,821,594 | 4/1989 | Rosheim et al. | 74/479 |
| 4,848,179 | 7/1989 | Ubhayakar | 74/479 |
| 4,862,759 | 9/1989 | Trevelyan et al. | 901/29 X |
| 4,878,393 | 11/1989 | Duta et al. | 74/479 |
| 4,911,033 | 3/1990 | Rosheim et al. | 74/479 |
| 5,036,724 | 8/1991 | Rosheim | 74/479 |
| 5,101,681 | 4/1992 | Shpigel | 74/479 |

OTHER PUBLICATIONS

Brochure Entitled "Ross-Hime Designs".

Primary Examiner—Rodney H. Bonck
Assistant Examiner—Ryan W. Massey

[57] ABSTRACT

A mechanical joint includes a mechanism for effecting pitch and yaw, the effecting mechanism being attached to a housing support, a yaw drive mechanism slidably engaging the housing support, a pitch drive mechanism slidably engaging the housing support and a mechanism to actuate the yaw drive mechanism and the pitch drive mechanism, In accordance with the present invention, a unitary guide mechanism attached to the housing stabilizes movement of the yaw drive mechanism and the pitch drive mechanism by receiving at least a portion of the yaw drive mechanism and the pitch drive mechanism.

32 Claims, 8 Drawing Sheets

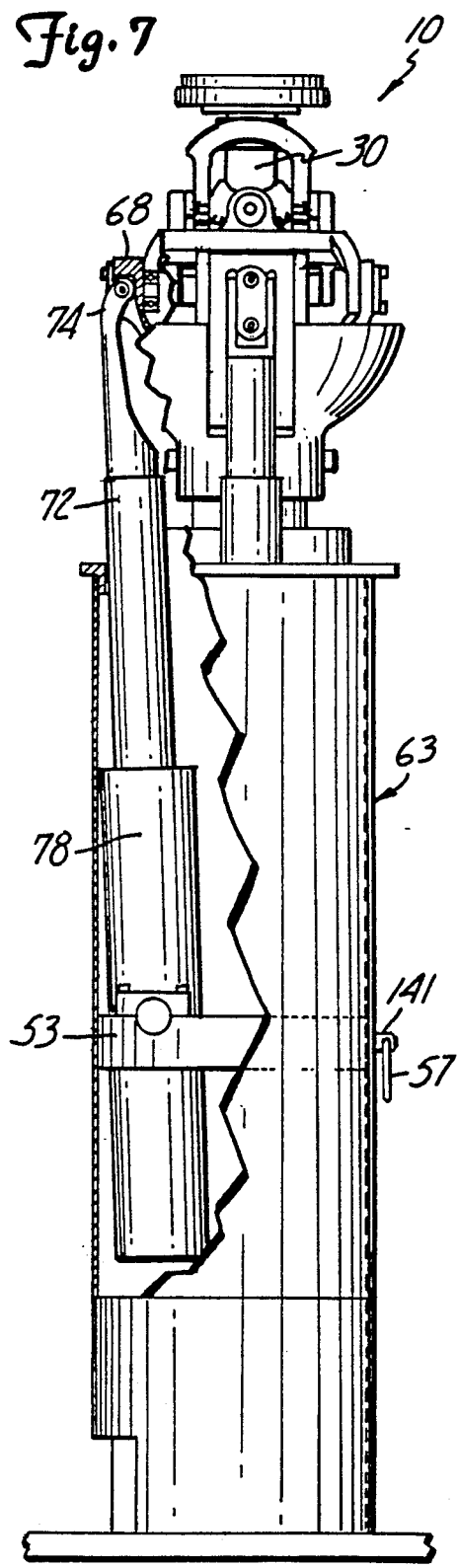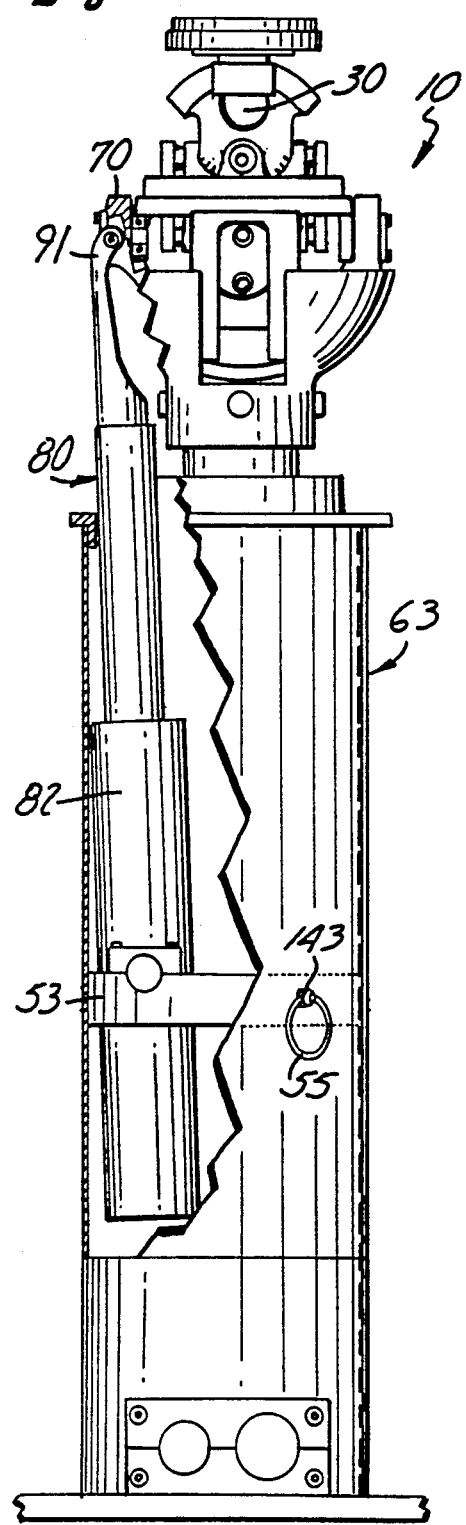

MODULAR ROBOT WRIST

BACKGROUND OF THE INVENTION

The present invention relates to mechanical joints and robot wrists, and in particular, it relates to mechanical joints and robot wrists having compound pitch/yaw motion capabilities.

Interest in robotics and the use of robots in industrial applications has greatly increased in recent years. One area in which the use of robots has become important is the replacement of humans in tasks that involve manual work, such as welding, material handling, paint spraying and assembly. Many of these tasks require working in cramped spaces or performing complex maneuvers. To perform such tasks, a robot arm or wrist should be able to rotationally move in a range similar to a human wrist and at a dwell time acceptable for the particular task involved.

Robot arms, wrists and joints are known in the art. One book reviewing the development of robot arms and wrists is entitled, *Robot Wrist Actuators*, John Wiley & Sons, Inc., 1989, and was written by the applicant of the present application. In the book, several characteristics are described that make robot wrists attractive. One characteristic is that a mechanical arm or wrist can be safely used in areas where there is a danger of explosion if the wrist is driven by electric actuators. However, there are several disadvantages with the prior art robot arms and wrists. Some of the disadvantages are also enumerated in the above-mentioned article and include large and bulky mechanical joints, singularity-ridden kinematics and low mechanical efficiency.

The Rosheim U.S. Pat. No. 5,036,724, issued to the applicant of the present application, overcame many of the disadvantages mentioned above. The robot wrist of the Rosheim '724 patent describes a mechanical joint having first and second gimbals for effecting pitch and yaw, the first and second gimbals being rotatably attached to a housing support, a yaw drive mechanism in slidable engagement with the housing support, a pitch drive mechanism in slidable engagement with the housing support and a mechanism to actuate the yaw drive mechanism and the pitch drive mechanism. Rollers engaging the surfaces of the yaw and pitch drive mechanisms stabilize the movement of the yaw and pitch drive mechanisms.

The wrist as described in the Rosheim '724 patent was greatly reduced in size compared to the mechanical joints of the prior art. At the same time, dexterity and mechanical efficiency were substantially increased. Over a period of time, however, the adverse conditions under which many of the mechanical joints are operating will affect the rollers which stabilize the movement of the yaw and pitch drive mechanisms. When the rollers are damaged or otherwise impaired by wear or use, the rollers need replacement. Frequent replacement of the rollers increases costs and downtime. Therefore, it is beneficial to maintain stabilization of the movement of the yaw and pitch drive mechanisms without the need for frequent replacement of the stabilizing mechanisms.

SUMMARY OF THE INVENTION

The present invention provides an improvement to a mechanical joint of the type generally described above including a mechanism for effecting pitch and yaw, the effecting mechanism being attached to a housing, a yaw drive mechanism slidably engaging the housing, a pitch drive mechanism slidably engaging the housing and a mechanism to actuate the yaw drive mechanism and the pitch drive mechanism. In the improvement of the present invention, a unitary guide mechanism is provided for stabilizing movement of the yaw drive mechanism and the pitch drive mechanism. The unitary guide mechanism preferably includes a four-armed guide having grooves in each of the arms for receiving at least a portion of the yaw drive mechanism and at least a portion of the pitch drive mechanism.

BRIEF DESCRIPTION OF THE DRAWINGS

FIG. 7 is a fragmented elevational view of a modular robot wrist made according to the present invention with a portion section and parts broken away;

FIG. 8 is a fragmented elevational view of a modular robot wrist made according to the present invention rotated 90° from the view of FIG. 7 with a portion in section and parts broken away;

DETAILED DESCRIPTION OF THE PREFERRED EMBODIMENTS

Figure 1:
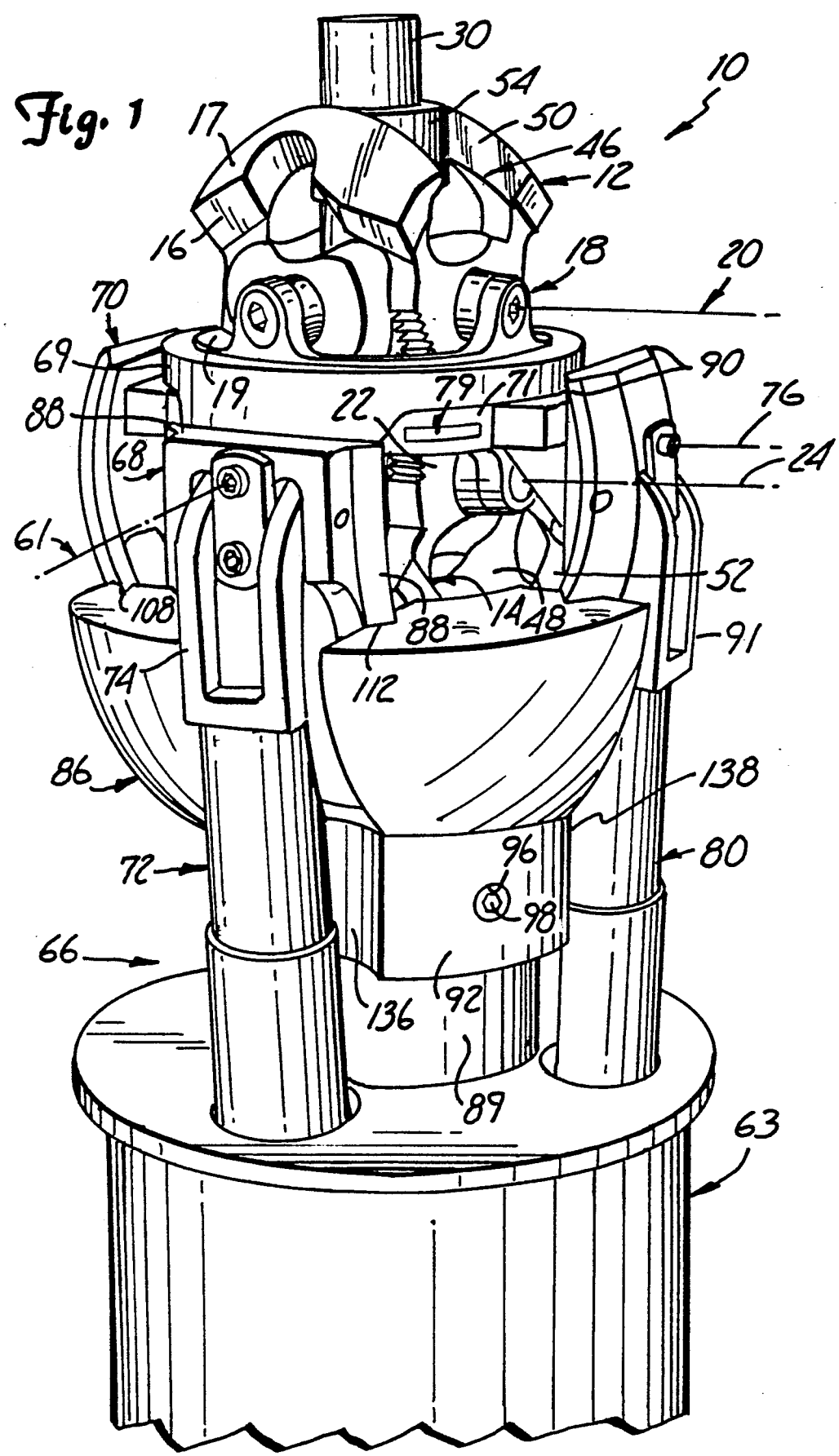
FIG. 1 is a perspective view of the modular robot wrist of the present invention.

The wrist of the present invention is generally indicated at 10 in FIG. 1. In addition to the improvement of the present invention, the drawings illustrate a typical wrist with the wrist 10 being substantially as described in U.S. Pat. No. 5,036,724, issued to the applicant of the present specification and which is hereby incorporated herein by reference.

The wrist 10 includes an upper gimbal assembly 12, a lower gimbal assembly 14 and a housing 18. The reference to upper and lower gimbal assemblies is for purposes of convenience with respect to the drawings and is not intended to limit the present invention in any way.

The housing 18 includes an annular member 19 surrounding at least a portion of the upper gimbal assembly 12 and the lower gimbal assembly 14. Attachment of the upper gimbal assembly 12 and the lower gimbal assembly 14 to the housing 18 is discussed further below.

The upper gimbal assembly 12 includes an outer upper gimbal 16 rotatably and pivotally attached to the housing 18 along a pivot axis 20, as best illustrated in FIG. 1. The lower gimbal assembly 14 includes an outer lower gimbal 22 rotatably and pivotally attached to the housing 18 about a pivot axis 24.

Figure 3:
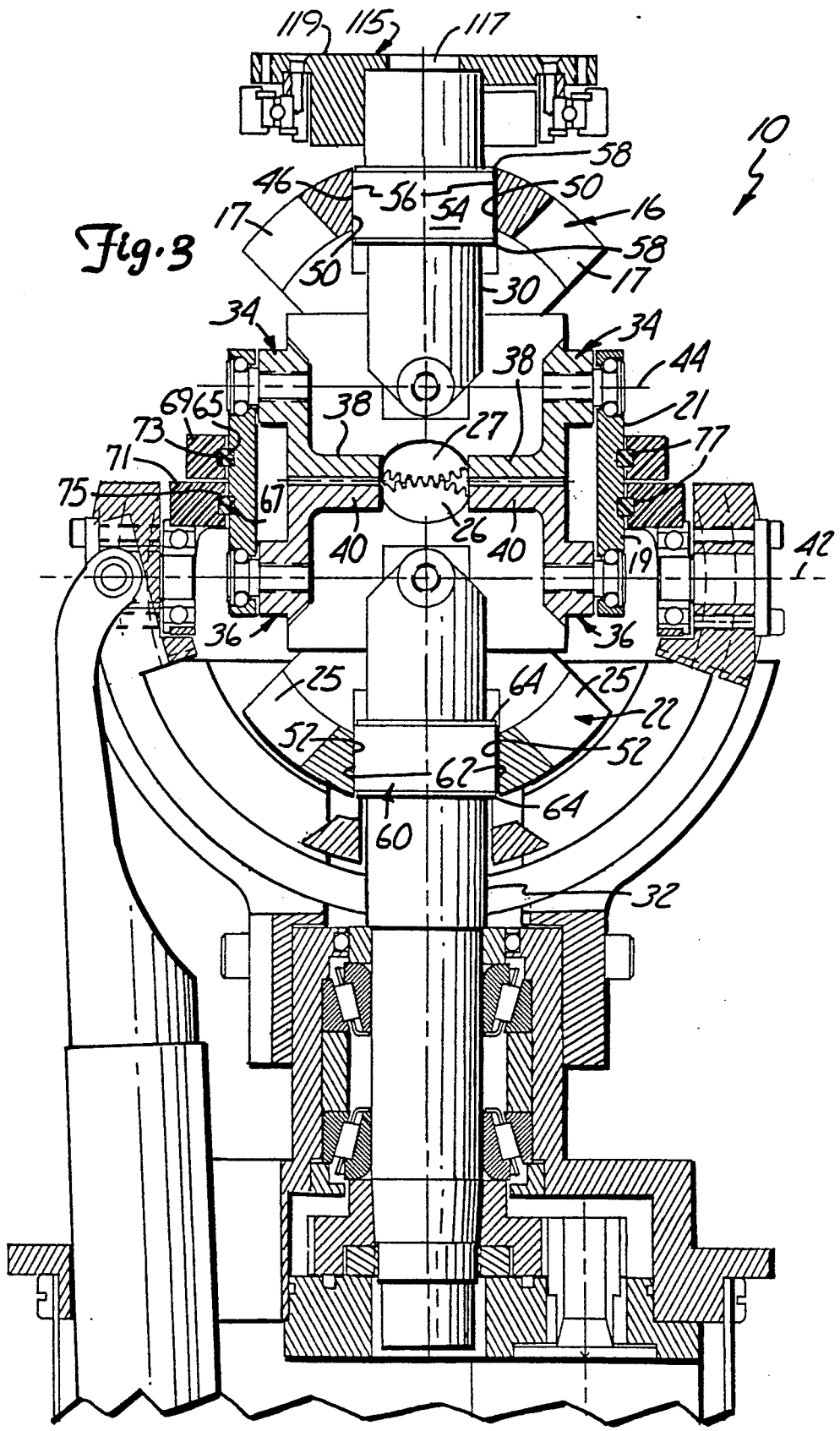
FIG. 3 is a sectional view of the modular robot wrist of the present invention rotated 90° from the view of FIG. 2.

As illustrated in FIGS. 1 and 3, the outer upper gimbal 16 and the outer lower gimbal 22 further include a plurality of lobes 17 and 25, respectively, protruding outward therefrom. The lobes 17 and 25 protrude outward from the outer upper and outer lower gimbals 16 and 22, respectively. The lobes 17 and 25 provide additional strength to the outer upper gimbal 16 and the outer lower gimbal 22, respectively, by stiffening the structure of the outer upper gimbal 16 and the outer lower gimbal 22.

As best illustrated in FIG. 3, the outer upper gimbal 16 includes a pair of spur gears 27. Similarly, the outer lower gimbal 22 includes a pair of spur gears 26 that are in cooperative engagement with the spur gears 27 of the outer upper gimbal 6 such that motion is transmitted between the outer upper gimbal 16 and outer lower gimbal 22 through the spur gears 27 and 26. Movement of the outer upper and lower gimbals 16 and 22 causes "yaw" motion in the wrist 10.

Figure 2:
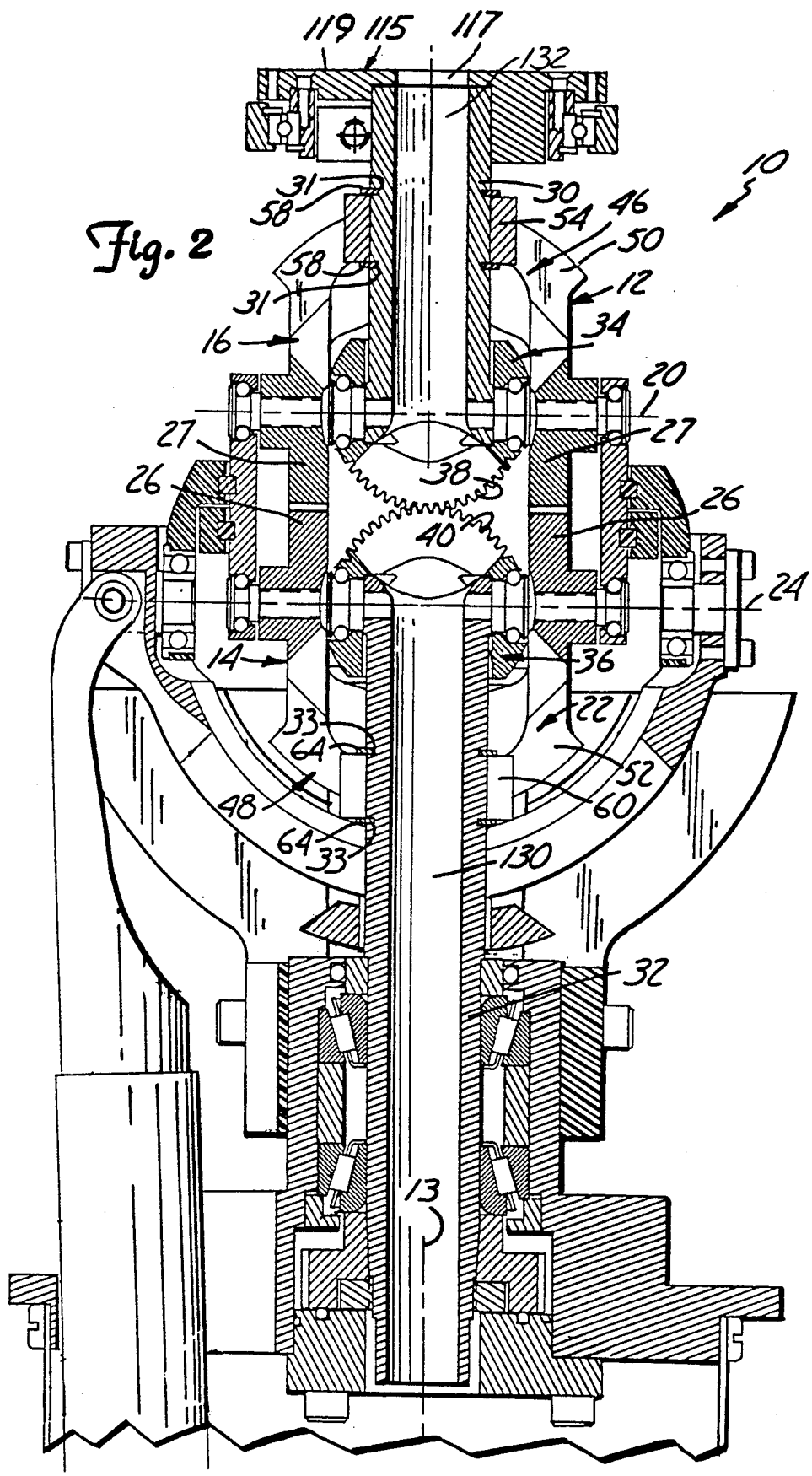
FIG. 2 is a sectional view of the modular robot wrist of the present invention.

To accomplish movement of the wrist in a direction essentially perpendicular to the axes 20 and 24 ("pitch" motion), the wrist includes upper and lower drive shafts 30 and 32 attached to upper inner gimbal 34 and lower inner gimbal 36, respectively, as illustrated in FIG. 2. The upper inner gimbal 34 includes spur gears 38. Similarly, the lower inner gimbal 36 includes spur gears 40 that mate and cooperate with the spur gears 38 permitting pivoting of the wrist about axis 42 and the upper drive shaft 30 about axis 44 as best illustrated in FIG. 3.

As illustrated in FIG. 2, the upper outer gimbal 16 and the lower outer gimbal 22 include slots 46 and 48, respectively, through which the drive shafts 30 and 32, respectively, extend. To facilitate movement within the slots 46 and 48, the slot 46 includes a first guide surface 50 and the slot 48 includes a second guide surface 52. Although only one guide surface of the upper outer and lower outer gimbals 16 and 22 is illustrated, it will be understood that a second oppositely facing surface with a like guide surface exists.

As illustrated in FIG. 3, a guide member 54 is releasably disposed about the upper drive shaft 30 to permit movement of the upper drive shaft 30 within the slot 46 with minimal backlash. The guide member 54 includes a pair of outwardly facing, substantially flat surfaces 56 which engage the guide surfaces 50, as illustrated in FIG. 3. To releasably secure the guide member 54 about the upper drive shaft 30, the upper drive shaft 30 includes a pair of annular grooves 31 with one annular groove positioned on each side of the guide member 54 as illustrated in FIG. 2. A locking ring 58 is releasably secured within each of the annular grooves 31 to maintain the guide member 54 in a releasably secured position about the upper drive shaft 30.

In FIG. 3, a guide member 60 is likewise releasably disposed about the lower drive shaft 32 in a similar fashion. The guide member 60 permits movement of the lower outer gimbal 22 about the lower drive shaft 32. The guide member 60 includes a pair of outward facing, substantially flat surfaces 62 which engage the guide surfaces 52. To releasably secure the guide member 60 about the lower drive shaft 32, the lower drive shaft 32 includes a pair of annular grooves 33 with one annular groove positioned on each side of the guide member 60 as illustrated in FIG. 2. A locking ring 64 is releasably secured within each of the annular grooves 33 to maintain the guide member 60 in a releasably secured position about the lower drive shaft 32.

Guide members 54 and 60 are preferably constructed of a self-lubricating plastic such as the type sold under the trademark ERDALITE by Du Pont deNemours, E. I., & Co. of Wilmington, Del. In addition, glass-filled or polyetrafluoroethylene impregnated self-lubricating plastic can also be utilized.

In FIG. 2, the cooperation between the lower drive shaft 32 and the upper drive shaft 30 through the respective gears 38 and 40 provides movement (pitch movement) of the upper drive shaft 30 from a position that is coaxial to the lower drive shaft 32 to a position that is essentially perpendicular to the lower drive shaft 32. It will be understood that the upper drive shaft 30 is movable in exactly an opposite direction for 90° or a total of 180°. As illustrated in FIG. 3, movement in a direction perpendicular to the pitch movement (yaw movement) is caused by outer gimbals 16 and 22 through their respective gears 27 and 26. If both inner gimbals 34 and 36 and outer gimbals 16 and 22 are actuated simultaneously, a compound yaw/pitch motion results.

Motive force to the wrist 10 is provided by a drive mechanism generally indicated at 66 in FIG. 1. The drive mechanism 66 transfers motive force from a plurality of drive motors disposed within a motor housing 63 to the wrist 10. The drive mechanism 66 includes a yaw drive gimbal 68, a pitch drive gimbal 70 and the previously mentioned lower drive shaft 32.

The yaw drive gimbal 68 is pivotally attached to a yaw attachment collar 69 and the pitch drive gimbal 70 is pivotally attached to a pitch attachment collar 71 The yaw attachment collar 69 and the pitch attachment collar 71 are in circumferential slidable engagement with the housing 18 as described further below.

Figure 4:
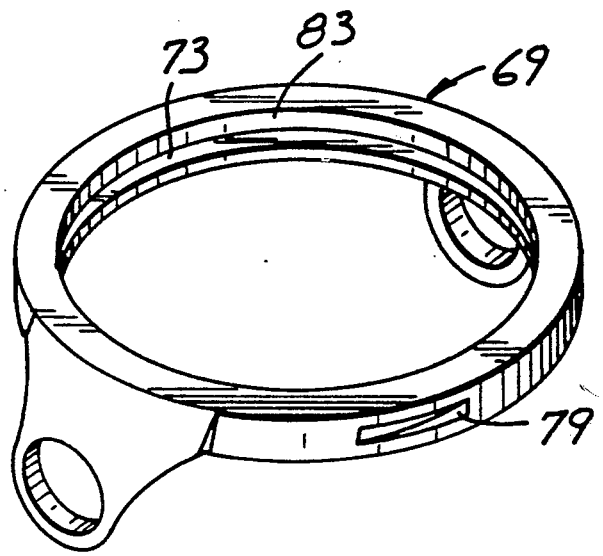
FIG. 4 is a perspective view of a yaw drive mechanism attachment collar.
Figure 5:
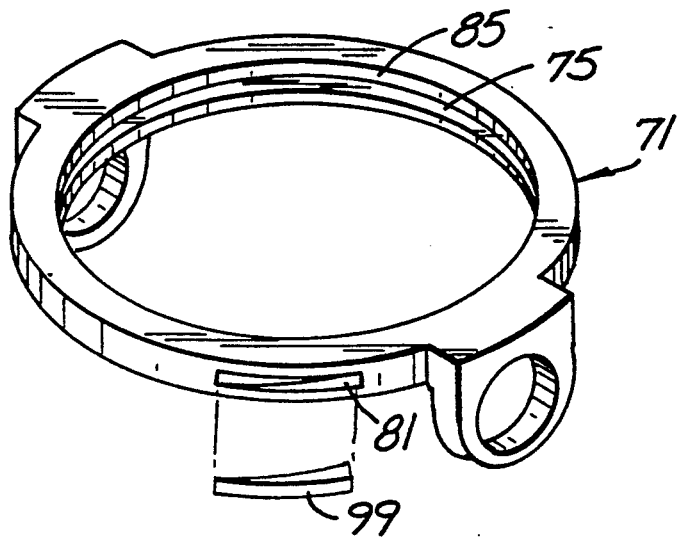
FIGS. 5 is a perspective view of a pitch drive mechanism attachment collar.

As best illustrated in FIGS. 4 and 5, the yaw attachment collar 69 includes a groove 73 extending substantially around an entire inner surface 83 of the yaw attachment collar 69. The pitch attachment collar 71 includes a groove 75 extending substantially around an entire inner surface 85 of the pitch attachment collar 71.

Figure 6:
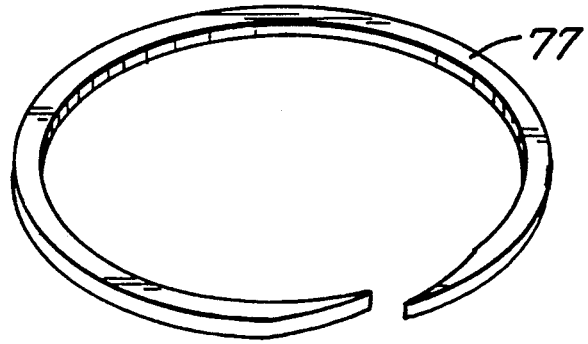
FIG. 6 is a perspective view of a locking split ring which releasably secures the attachment collars to the support housing.

As illustrated in FIG. 6, a substantially circular split ring 77 is provided. As illustrated in FIG. 3, one split ring 77 is positioned in each of the grooves 73 and 75 and a corresponding pair of grooves 65 and 67 in an outer surface 21 of the housing 18 to releasably secure the attachment collars 69 and 71 to the housing 18 in a slidably engaging manner. In FIGS. 4 and 5, an aperture 79 and 81 in the attachment collars 69 and 71, respectively, allows the split ring 77 to be inserted into and removed from the grooves 65 and 67 of the housing 18 and the grooves 73 and 75 of the attachment collars 69 and 71 without the need for disassembly of the entire wrist 10.

As illustrated in FIG. 5, a plug element 99 is inserted into the aperture 81 subsequent to the insertion of the split ring 77 into the grooves 65 and 67. The plug element 99 is sized to fit snugly within the aperture 81 and prevents debris and other unwanted substances from entering the grooves 65 and 67 and interfering with the action of the attachment collars 69 and 71.

As illustrated in FIGS. 7 and 8, motive force is imparted to the yaw drive gimbal 68 through an electrically actuated yaw push-pull rod 72 and to the pitch drive gimbal 70 through an electrically actuated push-pull rod 80. The rod 72 is pivotally attached to a plate support member 53 which is releasably secured to the motor housing 63 by a pin 141. The rod 80 is also pivotally attached to the plate support member 53 which is releasably secured to the motor housing 63 by a pin 143. The pin 141 extends through an aperture (not shown) in the motor housing 63 and an aperture (not shown) in the plate support member 53. The pin 143 extends through an aperture (not shown) in the motor housing 63 and an aperture (not shown) in the plate support member 53. The pins 141 and 143 are preferably of the type which include a spring loaded ball in one end thereof which, upon being inserted, rests within a detente in the plate member aperture. Although described as including a pin having a spring loaded ball at one end, any type of pin fastening mechanism is within the scope of the present invention.

The pins 141 and 143 are designed to be easily insertable and removable from their connection with the motor housing 63 and the plate support member 53. Rings 57 and 55 are pivotally mounted to one end of the pins 141 and 143, respectively, to permit the pins 141 and 143 to be grasped easily by another mechanical joint without requiring human workers to enter the working area of the wrist 10. With the releasable pins 141 and 143 as described above, any malfunction by either of the push-pull rods 72 and 80 which renders either or both of the push-pull rods 72 and 80 inoperable can be overcome by disconnecting the push-pull rods 72 and 80 from the motor housing 63 thereby allowing the wrist 10 to operate in the remaining operable directions.

As illustrated in FIG. 1, the push-pull rod 72 further includes an upper end portion 74 which is pivotally attached to the yaw drive gimbal 68 such that the yaw drive gimbal 68 pivots about an axis 76. An electric motor 78, as illustrated in FIG. 7, is disposed within the motor housing 63 and provides motive force to the yaw push-pull rod 72.

Similarly, as illustrated in FIG. 1, the push-pull rod 80 further includes an upper end portion 91 pivotally attached to the pitch drive gimbal 70 such that the pitch drive gimbal 70 pivots about the axis 61. An electric motor 82, as illustrated in FIG. 8, is disposed within the motor housing 63 and provides motive force to the pitch push-pull rod 80.

In addition, as illustrated in FIG. 1, the yaw drive gimbal 68 is arcuately shaped whereupon actuation of the yaw push-pull rod 72 causes the yaw drive gimbal 68 to pivot about the axis 76 thereby providing yaw movement of the wrist 10. Furthermore, the pitch drive gimbal 70 is arcuately shaped whereupon actuation of the pitch push-pull rod 80 causes the pitch drive gimbal 70 to pivot about the axis 61 thereby providing pitch movement of the wrist 10. Actuation of both the yaw push-pull rod 72 and the pitch push-pull rod 80 provides a compound pitch-yaw movement of the wrist 10 of the present invention.

In FIG. 2, rotational movement is imparted to the wrist 10 through rotation of the drive shaft 32 by yet another motor (not shown). Rotation of the drive shaft 32 causes the lower gimbal assembly 14 to rotate about an axis 13 thereby imparting rotational movement to the upper gimbal assembly 12.

As illustrated in FIG. 1, to minimize backlash and facilitate precision movement, a unitary guide mechanism 86 is mounted on the housing 18. The yaw drive gimbal 68 includes oppositely facing arcuate edges 88 that are received by the guide mechanism 86. Similarly, the pitch drive gimbal 70 includes oppositely facing arcuate edges that are received by the guide mechanism 86. The guide mechanism 86 is positioned such that the yaw drive gimbal 68 and the pitch drive gimbal 70 are seated in the guide mechanism 86 and slidably engage the guide mechanism 86.

Figure 9:
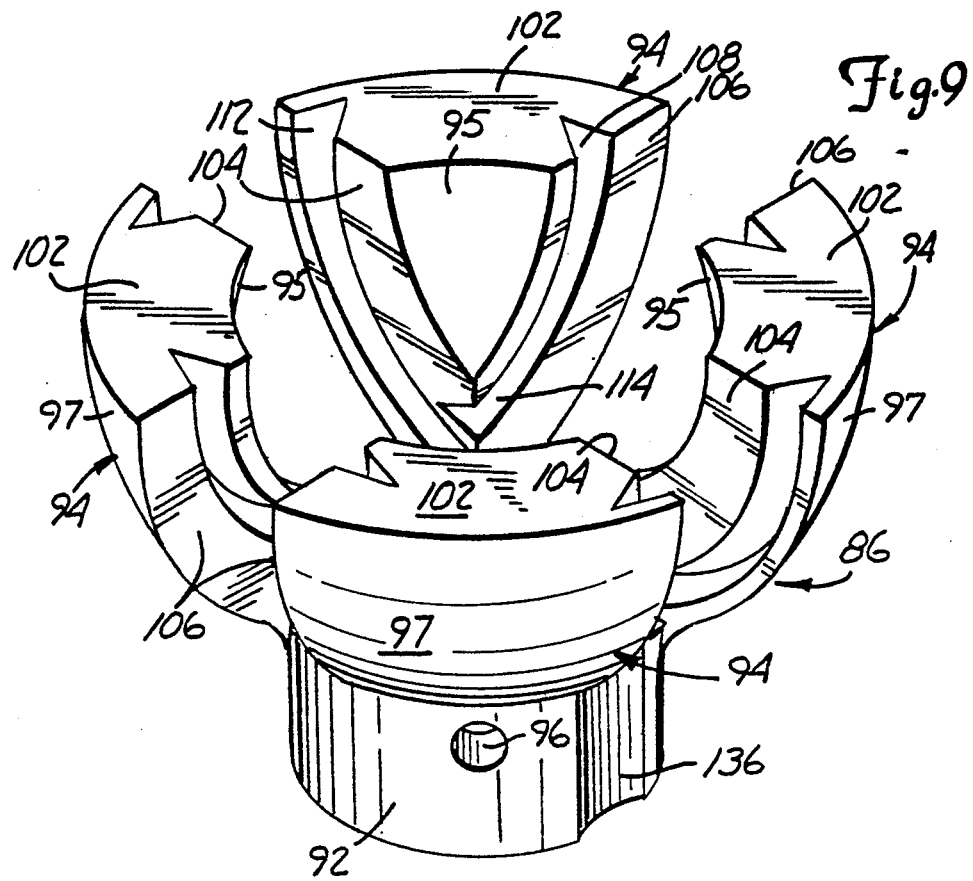
FIG. 9 is a perspective view of a unitary guide mechanism for stabilizing movement of the yaw drive mechanism and the pitch drive mechanism.
Figure 10:
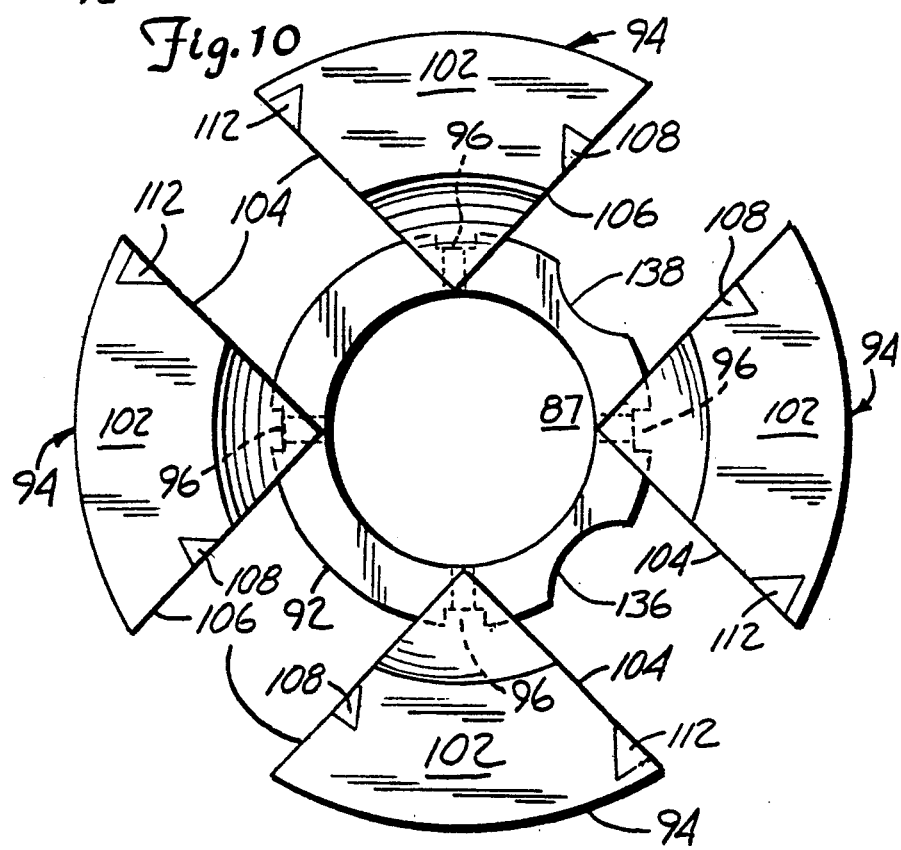
FIG. 10 is a top view of a unitary guide mechanism for stabilizing movement of the yaw drive mechanism and the pitch drive mechanism.

As illustrated in FIG. 9, the guide mechanism 86 includes a hollow base portion 92 and a plurality of arms 94. As illustrated in FIG. 10, the base portion has a central opening 87. In FIG. 1, the base portion 92 is placed over a mounting member 89 extending upward from the motor housing 63 such that the mounting member 89 is received within the opening 87.

As illustrated in FIG. 10, the base portion 92 further includes four apertures 96 with one aperture 96 positioned beneath each arm 94. As illustrated in FIG. 1, each of the apertures 96 receives a bolt 98 (only one aperture 96 and one bolt 98 is shown in FIG. 1. The bolts 98 extend through the apertures 96 in the base portion 92 and are threaded into corresponding threaded apertures (not shown) formed in the mounting member 89. Although the guide mechanism 86 is illustrated as being mounted to the mounting member 89 by four bolts 98, it is within the scope of the present invention to mount the guide mechanism 86 to the mounting member 89 with any number of bolts through an equal number of apertures or in any other conventional manner.

As illustrated in FIGS. 9 and 10, each of the arms 94 include an arcuate inner and outer surface 95 and 97. In addition, each of the arms extend substantially upward from the base portion 92. In the preferred embodiment, there are four arms with each arm being equally spaced from each adjacent arm around the base portion 92.

Each of the arms 94 includes a top surface 102 and a pair of side surfaces, namely a yaw side surface 104 and a pitch side surface 106. The yaw side surfaces 104 of adjacent arms 94 face each other. Likewise, the pitch side surfaces 106 of adjacent arms 94 face each other.

To receive the yaw drive gimbal 68, an arcuate yaw groove 112 is disposed in the yaw side surface 104 of each of the arms 94. Each yaw groove 112 extends from a point (now shown) near the base portion 92 and through the top surface 102. As illustrated in FIG. 1, at least a portion of the outer edges 88 of the yaw drive gimbal 68 is slidably received within each of the yaw grooves 112 thereby allowing the outer edges 88 to travel within the yaw groove 112.

Having at least a portion of the outer edges 88 of the arcuate yaw drive gimbal 68 slidably within the arcuate yaw grooves 112 facilitates precision movement of the yaw drive gimbal 68 by allowing the yaw drive gimbal 68 to move smoothly without any backlash relative to the guide mechanism 86. As the push-pull rod 72 moves the upper end portion 74 and thus, the yaw drive gimbal 68, the outer edges 88 of the yaw drive gimbal 68 will follow in the arcuate yaw grooves 112. As mentioned above, this movement of the yaw drive gimbal 68 causes the yaw drive gimbal 68 to pivot relative to the housing 18 about the axis 76.

As illustrated in FIG. 9, to receive the pitch drive gimbal 70, an arcuate pitch groove 108 is disposed in the pitch side surface 106 of each of the arms 94. Each pitch groove 108 extends from a point 114 near the base portion 92 and through the top surface 102. At least a portion of the outer edges 90 of the pitch drive gimbal 70 is slidably received within each of the pitch grooves 108 as illustrated in FIG. 1 thereby allowing the outer edges 90 to travel within the pitch grooves 108.

Having at least a portion of the arcuate pitch drive gimbal 70 slidably within the arcuate pitch grooves 108 facilitates precision movement of the pitch drive gimbal 70 by allowing the pitch drive gimbal 70 to move smoothly without any backlash relative to the guide mechanism 86. As the push-pull rod 80 moves the upper end portion 91 and thus, the pitch drive gimbal 70, the outer edges 90 of the pitch drive gimbal 70 will follow in the arcuate pitch grooves 108. As mentioned above, this movement of the pitch drive gimbal 70 causes the pitch drive gimbal 70 to pivot relative to the housing 18 about the axis 61.

As illustrated in FIGS. 9 and 10, the base portion 92 further includes a pair of channels 136 and 138. The channel 136 is formed in the base portion 92 between two of the yaw side surfaces 104; the channel 138 is formed in the base portion 92 between two of the pitch side surfaces 106. In FIG. 1, as the yaw push-pull rod 72 pushes the connection point between the yaw drive gimbal 68 and the upper end portion 74 of the push-pull rod 72 away from the motor housing 63, the push-pull rod 72 will tend to move closer to the base portion 92 and be received within the channel 136. Likewise, as the pitch push-pull rod 80 pushes the connection point between the pitch drive gimbal 70 and the upper end portion 91 of the pitch push-pull rod 80 away from the motor housing 63, the push-pull rod 80 will tend to move closer to the base portion 92 and be received within the channel 138.

The guide mechanism 86 is preferably constructed of a self-lubricating plastic. One suitable material is sold under the trademark ERDALITE by Du Pont deNemours, E. I., & Co. of Wilmington, Del. Other suitable materials include self-lubricating plastic which is glass-filled or polyetrafluoroethylene impregnated. In addition, the self-lubricating plastic can be molded around a steel frame or other type frame to provide additional strength to the arms 94.

As illustrated in FIG. 2, the lower drive shaft 32 includes an inner passage 130 and the upper drive shaft 30 also includes an inner passage 132. The passages 130 and 132 are open at their gear end portions and permit placement of wires, fiber optic lines, fluid or pneumatic lines for use at the distal end of the drive shaft 32.

As illustrated in FIGS. 2 and 3, an adapter plate 115 can be releasably secured to the distal end of the upper drive shaft 30 in a known manner. The adapter plate 115 includes a mounting surface 119 and an aperture 117 extending therethrough. The mounting surface 119 is designed for attaching various tools and implements, such as a gripper and other end-effectors (not shown). The aperture 117 receives the electrical wires, fiber optic cables, fluid or pneumatic lines extending from the upper drive shaft 30.

Figure 11:
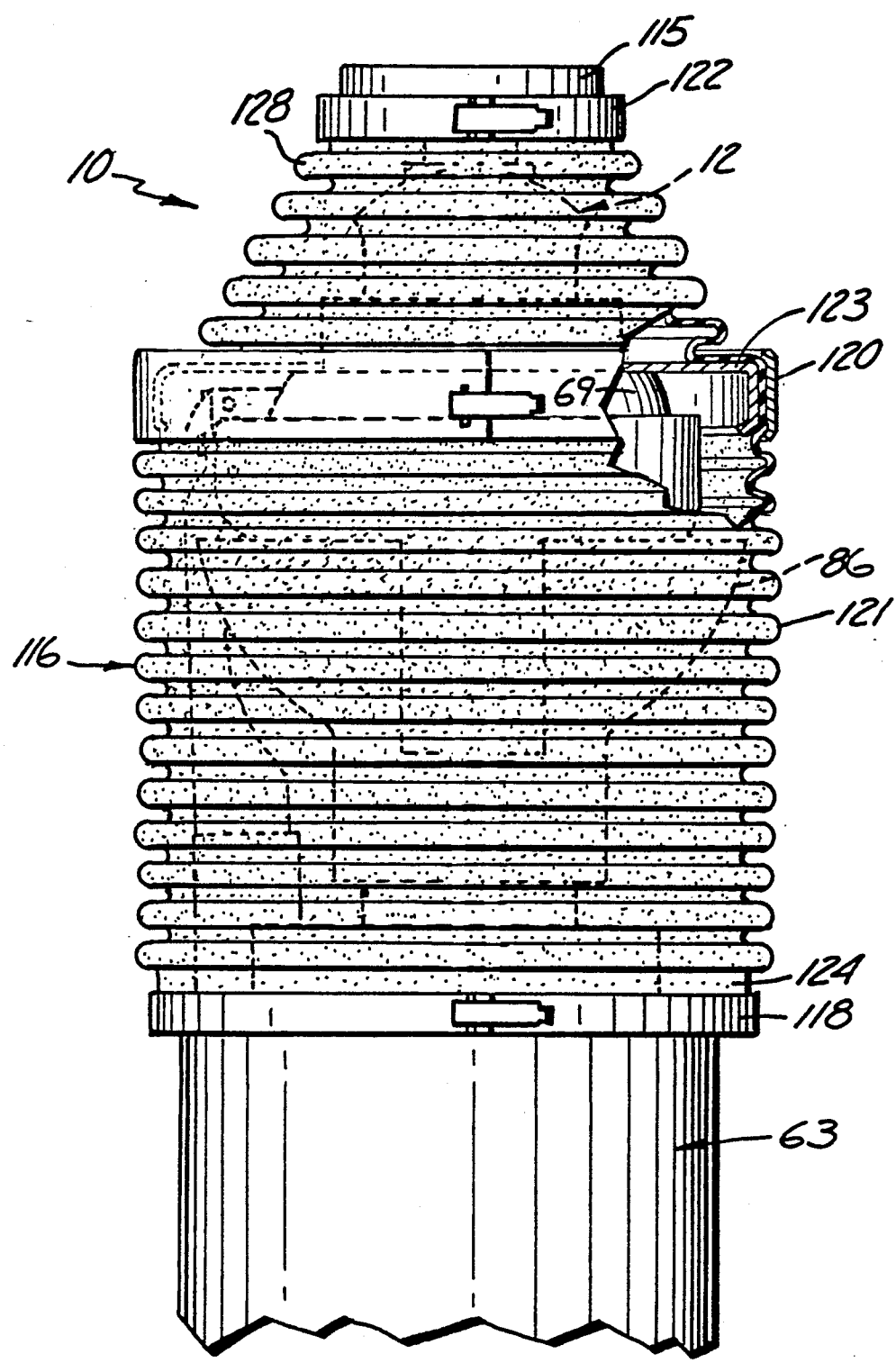
FIG. 11 is an elevational view of a sleeve member with a portion of the robot wrist being illustrated in phantom.

As illustrated in FIG. 11, a sleeve 116 is provided about the wrist 10 to block debris and other foreign substances from reaching the wrist 10. The sleeve 116 is preferably comprised of fabric reinforced, seamless rubber although other types of material are within the scope of the present invention.

The sleeve 116 includes a plurality of clamps 118, 120 and 122 positioned over an outer surface 121 of the sleeve 116 to releasably secure the sleeve 116 to the wrist 10. The clamps 118, 120 and 122 are designed to be easily opened and closed by use of another mechanical joint so that the sleeve 116 can be replaced or otherwise removed without requiring human workers to enter the working area of the wrist 10. Keeping humans out of the working area of the wrist 10 prevents potential contamination of the working environment of either the wrist 10 or the humans.

As mentioned above, a preferred embodiment of the present invention includes three clamps 118, 120 and 122. The first clamp 118 is positioned at a lower end portion 124 of the sleeve 116 and is sized to releasably clamp the sleeve 116 to the motor housing 63.

The second clamp 120 is positioned to releasably clamp the sleeve 116 to the wrist 10 over a flange 123. The flange 123 is preferably attached to the attachment collar 69 by a plurality of screws (not shown). In the preferred embodiment, the screws are equally spaced around the circumference of the attachment collar 69.

The third clamp 122 is positioned at an upper end portion 128 of the sleeve 116 and is sized to releasably clamp the sleeve 116 to the adapter plate 115. It should be noted that although the sleeve 116 is described as being clamped to the wrist 10 by clamps 118, 120 and 122, it is within the scope of the present invention to use other attachment means to clamp the sleeve 116 to the wrist 10.

Figure 12:
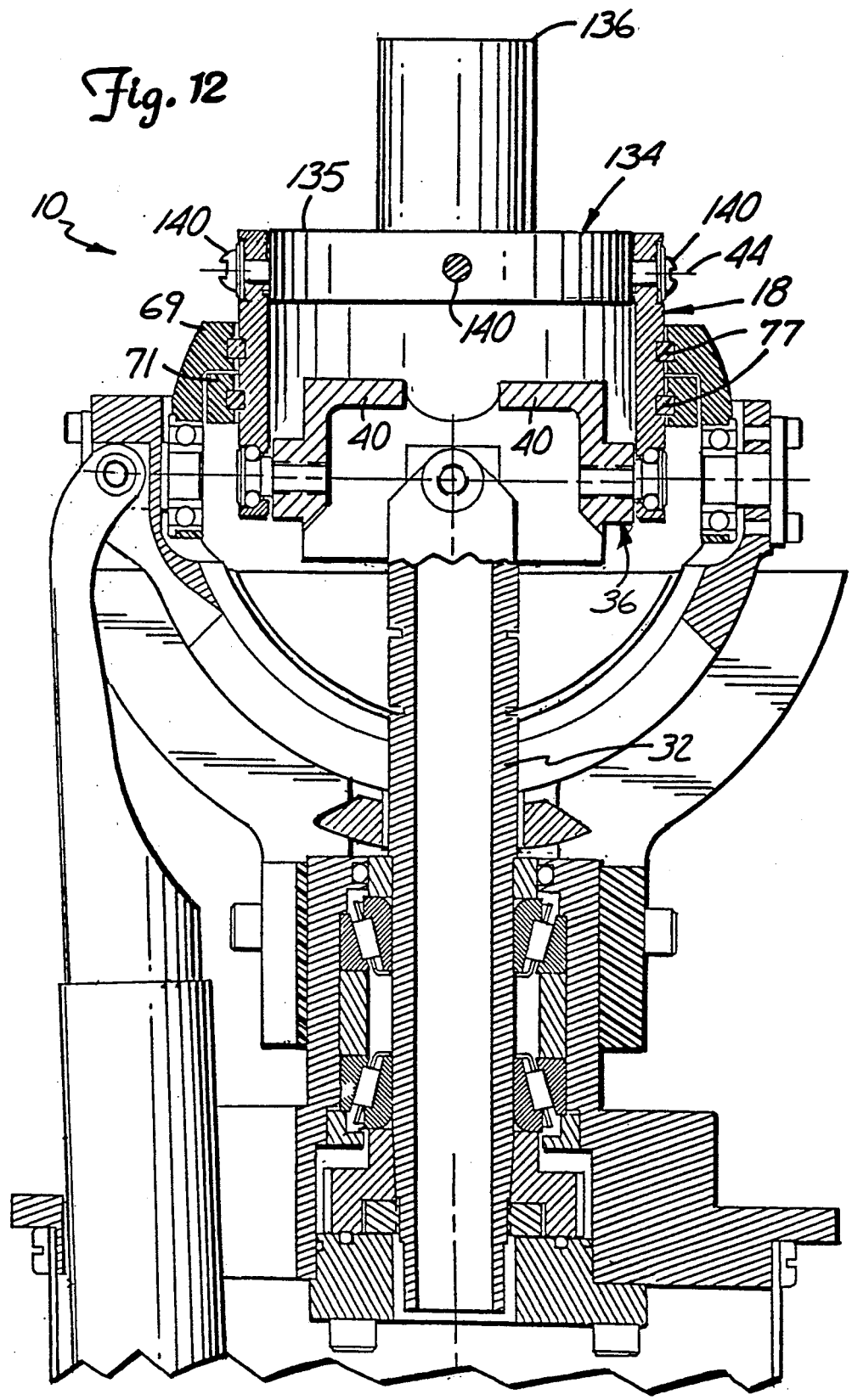
FIG. 12 is an elevational view of yet another embodiment of the wrist of the present invention with a portion illustrated in section with a lower gimbal assembly rotated 90° from the view of FIG. 2.

In another embodiment of the present invention as illustrated in FIG. 12, the wrist 10 can be modified to add a tool plate 134. The tool plate 134 includes a mounting surface 135 for attaching tools and implements, such as a gripper and other end-effectors (not shown). The type of tools and implements used will depend directly on the intended use and application of the wrist 10.

In addition, the tool plate 134 includes an aperture 136. The aperture 136 is provided for receiving the electrical wires, fiber optic cables, fluid or pneumatic lines extending from the lower drive shaft 32.

To add the tool plate 134, the upper gimbal assembly 12 (not shown in FIG. 12) is first removed from the upper gimbal assembly's 12 pivotal connection to the housing 18. Next, the outer lower gimbal assembly 14 is removed. The tool plate 134 is then releasably secured to the housing 18 by a plurality of screws 140. Although described as being attached to the housing 18 by a plurality of screws 140, it is within the scope of the present invention to attach the tool plate 135 to the wrist 10 by other attachment means.

Although similar to the adapter plate 115, as illustrated in FIGS. 2 and 3, the tool plate 134 illustrated in FIG. 12 allows the wrist 10 to apply approximately twice the torquing force to the attached tool implement with only one-half loss of mobility. The greater torquing force is a result of the wrist 10 no longer being a compound joint due to the reduced connections between the lower drive shaft 32 and the mounting surface 135 of the tool plate 134. Furthermore, With the upper gimbal assembly 12 (not shown in FIG. 12) removed, greater torque can be applied without concern for stripping of the spur gears 27 and 26 which connect the outer upper gimbal 16 and the outer lower gimbal 22, as illustrated in FIG. 3, and spur gears 38 and 40 which connect the inner upper gimbal 34 and the inner lower gimbal 36, as illustrated in FIG. 2.

Although the present invention has been described with reference to preferred embodiments, workers skilled in the art will recognize that changes may be made in form and detail without departing from the spirit and scope of the invention.

I claim:

1. In a mechanical joint of the type having means for effecting pitch and yaw, the means for effecting being attached to a housing support, yaw drive means slidably engaging the housing support, pitch drive means slidably engaging the housing support, means to actuate the yaw drive means and the pitch drive means, and unitary guide means for stabilizing movement of the yaw drive means and the pitch drive means, the unitary guide means being attached to the housing support wherein the yaw and pitch drive means slidably engage the guide means, the improvement comprising:

including first and second gimbal assemblies as part of the means for effecting pitch and yaw, with each gimbal assembly transferring motion to the other gimbal assembly so that yaw and pitch are effected.

2. The joint of claim 1 wherein the unitary guide means includes a base portion and a plurality of arms extending from the base portion, each of the arms having a pair of arcuate grooves, the arcuate grooves receiving either at least a portion of the yaw drive means or at least a portion of the pitch drive means thereby stabilizing movement of the yaw drive means and pitch drive means.

3. The joint of claim 1 wherein the unitary guide means is constructed of a self-lubricating plastic engaging a surface of the yaw drive means and a surface of the pitch drive means.

4. The joint of claim 1 and further including first guide means disposed about conduit means, the conduit means being attached to the first gimbal assembly and extending through a slot in the first gimbal assembly, the slot having oppositely-facing first and second surfaces engageable by the first guide means wherein the first guide means stabilize movement of the first gimbal assembly.

5. The joint of claim 4 and further including an adapter plate releasably secured to a distal end of the conduit means, the adapter plate including a mounting surface for attaching gripper and other end-effectors.

6. The joint of claim 4 wherein the first guide means includes self-lubricating plastic releasably secured about the conduit means.

7. The joint of claim 1 and further including second guide means disposed about drive means, the drive means being attached to the second gimbal assembly and extending through a slot in the second gimbal assembly, the slot having oppositely-facing first and second surfaces engageable by the second guide means wherein the second guide means stabilize movement of the second gimbal assembly.

8. The joint of claim 7 wherein the second guide means includes self-lubricating plastic releasably secured about the drive means.

9. The joint of claim 1 wherein the yaw drive means includes a first attachment collar and the pitch drive means includes a second attachment collar, the first and second attachment collars slidably engaging the housing, the yaw drive means being pivotally attached to the first attachment collar and the pitch drive means being pivotally attached to the second attachment collar.

10. The joint of claim 9 wherein the housing includes an outer surface having a second housing groove and the second attachment collar includes a second groove and a second inner surface, the second groove extending substantially around the second inner surface and further wherein a substantially circular second split ring is positioned in the second groove and the second housing groove to thereby releasably secure the second attachment collar to the housing in a slidably engaging manner.

11. The joint of claim 9 wherein the housing includes an outer surface having a first housing groove and the first attachment collar includes a first groove and a first inner surface, the first groove extending substantially around the first inner surface and further wherein a substantially circular split ring is positioned in the first groove and the first housing groove to thereby releasably secure the first attachment collar to the housing in a slidably engaging manner.

12. The joint of claim 1 and further including a motor housing for housing the means to actuate the yaw drive means and the pitch drive means.

13. The joint of claim 12 wherein the means to actuate the yaw drive means and the pitch drive means includes a yaw actuation means to actuate the yaw drive means and a pitch actuation means to actuate the pitch drive means, wherein the yaw actuation means is pivotally attached to the motor housing by a first quick release pin and wherein the pitch actuation means is pivotally attached to the motor housing by a second quick release pin.

14. The joint of claim 1 and further including a sleeve surrounding at least a portion of the joint for blocking debris from that portion of the joint surrounded by the sleeve.

15. The joint of claim 14 wherein the sleeve is constructed of fabric reinforced, seamless rubber.

16. The joint of claim 14 wherein the sleeve is releasably secured to the joint by a plurality of clamps.

17. The joint of claim 1 wherein the means for effecting pitch and yaw include a tool plate releasably secured to the housing, the tool plate including a mounting surface for attaching gripper and other end-effectors.

18. The joint of claim 1 wherein the first gimbal assembly and the second gimbal assembly each include a plurality of lobes protruding outward therefrom.

19. In a mechanical joint of the type having means for effecting pitch and yaw, the means for effecting being attached to a housing support, yaw drive means slidably engaging the housing support, pitch drive means slidably engaging the housing support, means to actuate the yaw drive means and the pitch drive means, and unitary guide means for stabilizing movement of the yaw drive means and the pitch drive means, the unitary guide means being attached to the housing support wherein the yaw and pitch drive means slidably engage the guide means, the improvement comprising:

including a base portion and a plurality of arms extending from the base portion as part of the unitary guide means, with each of the arms having a pair of arcuate grooves, the arcuate grooves receiving either at least a portion of the yaw drive means or at least a portion of the pitch drive means thereby stabilizing movement of the yaw drive means and pitch drive means.

20. The joint of claim 19 wherein the unitary guide means is constructed of a self-lubricating plastic engaging a surface of the yaw drive means and a surface of the pitch drive means.

21. The joint of claim 19 wherein the yaw drive means includes a first attachment collar and the pitch drive means includes a second attachment collar, the first and second attachment collars slidably engaging the housing, the yaw drive means being pivotally attached to the first attachment collar and the pitch drive means being pivotally attached to the second attachment collar.

22. The joint of claim 21 wherein the housing includes an outer surface having a first housing groove and the first attachment collar includes a first groove and a first inner surface, the first groove extending substantially around the first inner surface and further wherein a substantially circular split ring is positioned in the first groove and the first housing groove to thereby releasably secure the first attachment collar to the housing in a slidably engaging manner.

23. The joint of claim 21 wherein the housing includes an outer surface having a second housing groove and the second attachment collar includes a second groove and a second inner surface, the second groove extending substantially around the second inner surface and further wherein a substantially circular second split ring is positioned in the second groove and the second housing groove to thereby releasably secure the second attachment collar to the housing in a slidably engaging manner.

24. The joint of claim 19 and further including a motor housing for housing the means to actuate the yaw drive means and the pitch drive means.

25. The joint of claim 24 wherein the means to actuate the yaw drive means and the pitch drive means includes a yaw actuation means to actuate the yaw drive means and a pitch actuation means to actuate the pitch drive means, wherein the yaw actuation means is pivotally attached to the motor housing by a first quick release pin and wherein the pitch actuation means is pivotally attached to the motor housing by a second quick release pin.

26. The joint of claim 19 and further including a sleeve surrounding at least a portion of the joint for blocking debris from that portion of the joint surrounded by the sleeve.

27. The joint of claim 26 wherein the sleeve is releasably secured to the joint by a plurality of clamps.

28. The joint of claim 26 wherein the sleeve is constructed of fabric reinforced, seamless rubber.

29. The joint of claim 19 wherein the means for effecting pitch and yaw include a tool plate releasably secured to the housing, the tool plate including a mounting surface for attaching gripper and other end-effectors.

30. In a mechanical joint of the type having means for effecting pitch and yaw, the means for effecting being attached to a housing support, yaw drive means slidably engaging the housing support, pitch drive means slidably engaging the housing support and means to actuate the yaw drive means and the pitch drive means, the improvement comprising:

unitary guide means for stabilizing movement of the yaw drive means and the pitch drive means, the unitary guide means being attached to the housing support wherein the yaw and pitch drive means slidably engage the guide means wherein the yaw drive means includes a first attachment collar and the pitch drive means includes a second attachment collar, the first and second attachment collars slidably engaging the housing, the yaw drive means being pivotally attached to the first attachment collar and the pitch drive means being pivotally attached to the second attachment collar.

31. The joint of claim 30 and further including a motor housing for housing the means to actuate the yaw drive means and the pitch drive means.

32. The joint of claim 30 wherein the means to actuate the yaw drive means and the pitch drive means includes a yaw actuation means to actuate the yaw drive means and a pitch actuation means to actuate the pitch drive means, wherein the yaw actuation means is pivotally attached to the motor housing by a first quick release pin and wherein the pitch actuation means is pivotally attached to the motor housing by a second quick release pin.

* * * * *